United States Patent [19]

Miyahara et al.

[11] Patent Number: 4,769,474
[45] Date of Patent: Sep. 6, 1988

[54] PROCESS FOR PURIFYING TRYPTOPHANE

[75] Inventors: Shoichiro Miyahara; Toshio Matsumoto; Tooru Miyahara; Kazunari Nitta, all of Fukuoka, Japan

[73] Assignee: Mitsui Toatsu Chemicals, Inc., Tokyo, Japan

[21] Appl. No.: 847,194

[22] Filed: Apr. 2, 1986

[30] Foreign Application Priority Data

Apr. 10, 1985 [JP] Japan .................................. 60-74486
Mar. 18, 1986 [JP] Japan .................................. 61-58404

[51] Int. Cl.$^4$ .................. C07D 209/08; C07D 209/20
[52] U.S. Cl. .................................. 548/497; 548/469; 548/496
[58] Field of Search ........................ 548/497, 496, 469

[56] References Cited

U.S. PATENT DOCUMENTS 3,420,788  1/1969  Solms .................... 548/497
3,450,712  6/1969  Samejima et al. .................... 548/497
4,357,276  11/1982  Takasa et al. .................... 548/469

FOREIGN PATENT DOCUMENTS 1189265  8/1986  Japan .................................. 548/497

Primary Examiner—Glennon H. Hollrah
Assistant Examiner—David B. Springer
Attorney, Agent, or Firm—Albert L. Jeffers

[57] ABSTRACT

A process for purifying tryptophan so as to contain almost no unreacted indole and a process for recovering unreacted indole with a very high percentage are provided, the purification process comprising passing a reaction fluid of tryptophan prepared from indole as raw material by means of an enzyme function, through a porous type, cation exchange resin layer, to cause the ion exchange part of the resin to absorb tryptophan, while to cause the porous part of the resin to adsorb indole, followed by eluting only the tryptophan with an alkali or acid aqueous solution, and the recovery process comprising subjecting tryptophan to repeated treatments of adsorption onto and elution from the ion exchange part of the resin and regeneration followed by eluting indole adsorbed onto the porous part of the resin with a water-containing organic solvent miscible with water and isolating indole from the resulting elute.

4 Claims, No Drawings

PROCESS FOR PURIFYING TRYPTOPHANE

BACKGROUND OF THE INVENTION

1. Field of the Invention

This invention relates to a process for purifying tryptophan obtained from indole as its raw material according to an enzyme process. More particularly it relates to a process for obtaining tryptophan by separating unreacted indole contained in the resulting tryptophan so that the indole content in the tryptophan is restricted within 10 ppm, as well as a process for recovering the indole.

2. Description of the Prior Art

Tryptophans, particularly L-tryptophan, are one of indispensable amino acids and useful compounds used for pharmaceuticals, health foods, feeds, etc.

As processes for producing L-tryptophan, a fermentation process using glucose or the like as raw material, a semi-fermentation process using anthranilic acid or the like as raw material, and besides, a process for obtaining L-tryptophan by subjecting indole as raw material to an enzymatic condensation reaction with L-serine, a process for obtaining L-tryptophan by causing an enzyme to act on indole, pyruvic acid and ammonia, etc. have been known.

A problem raised in the process for obtaining tryptophan by subjecting indole as raw material to an enzymatic function is how to separate unreacted indole contained in the resulting enzyme reaction fluid containing tryptophan.

The reaction fluid usually contains 100 ppm or more of indole. Even when indole is contained in a slightest quantity, it gives off a peculiar bad smell. Thus it is necessary to reduce its content in the final product down to at most 10 ppm, and particularly when the product is used for feeds, down to about 3 ppm.

However, indole and tryptophan both have indole skeletone and are similar in chemical structure; hence indole has a strong adhesion to tryptophan so that it is impossible to eliminate indole down to a tolerable quantity even when a means such as washing of final crystals is employed.

Further, indole is a raw material of high cost, and hence unless it can be recovered, the cost of the product increases.

Thus, in the production of tryptophan using indole, the step of purifying tryptophan containing unreacted indole after completion of the reaction should be a process capable of completely removing other impurities and at the same time, efficiently separating and recovering indole from tryptophan.

Usually, as to the process for producing tryptophan, it has been obtained, e.g. by reacting indole with serine in the presence of an enzyme or a fungus body having a tryptophan synthase function in an aqueous medium in the vicinity of neutrality. However, the enzyme or fugus body contained in the thus obtained reaction fluid must be removed, and for removing the enzyme or fungus body, various processes have been employed such as a process of separating these substances by causing them to adsorb onto a solid substance such as active carbon, adsorptive silica gel or the like according to usual treating method for amino acid, a separation process by deposition by means of a centrifugal separator, a process for purifying amino acid by removing these impurities by means of ion exchange resins, non-polar, porous resins, or the like process.

For example, the official gazette of Japanese patent application laid-open No. Sho 56-73050/1981 discloses a process for purifying L-tryptophan by isolation with strongly acidic ion exchange resin of macroporous type.

According to these processes, however, it is impossible to separate indole from tryptophan.

Indole and tryptophan are both difficultly soluble in water; hence for example, if it is intended to dilute a slurry of tryptophan after completion of the reaction with a large quantity of water to prepare an aqueous solution of tryptophan, followed by treatment with active carbon to thereby remove unreacted indole by adsorption, then a large quantity of tryptophan is also adsorbed together with indole.

Further, if a usual gel type cation exchange resin is used as described in the above official gazette, the adsorbed aromatic or heteroaromatic amino acid is relatively difficult to elute. Thus if a cation exhange resin of porous type which is easy to elute the amino acids is used to purify tryptophan by adsorption and elution, then it is naturally considered that indole is also contained in the elute. In this case, in order to separate indole from the elute, it is necessary to add an organic solvent which is not miscible with water, such as benzene, toluene or the like, to the aqueous solution of the eluted tryptophan to extract indole into the organic solvent and separate it. According to such a process, however, troublesome operations such as solvent recovery are required and it is difficult to reduce the indole content down to a tolerable range of about 3 ppm.

SUMMARY OF THE INVENTION

A first object of the present invention is to provide tryptophan produced from indole as raw material and having an extremely low content of unreacted indole.

A second object of the present invention is to provide, in the enzymatic production process of tryptophan from indole as raw material, a purification process of the resulting tryptophan into the one containing almost no unreacted indole.

A third object of the present invention is to provide a process for recovering unreacted indole from the reaction fluid of tryptophan prepared from indole as raw material according to an enzyme process.

In order to achieve these objects, the present inventors have made extensive research, and as a result have found that when the reaction fluid of tryptophan containing unreacted indole is passed through a porous type, cation exchange resin layer, indole has an affinity with the resin, and surprisingly enough, indole is selectively adsorbed only onto the porous part of the resin layer, and yet even when tryptophan adsorbed onto the ion exchange part is eluted, almost no indole is contained in the elute, and further have found that as to the used resin, since a water-containing organic solvent is used when indole is eluted, it is possible to easily regenerate the resin only by washing with water, the resin after subjected to elution of indole and reuse the washed resin for separating tryptophan.

The present invention in a first aspect resides in:

a process for purifying tryptophan which comprises passing a reaction fluid of tryptophan prepared from indole as raw material by means of an enzyme function, through a porous type, cation exchange resin layer, to cause the ion exchange part of the resin to adsorb tryptophan thereonto, while to cause the porous part of the resin to adsorb indole thereonto, followed by eluting only tryptophan adsorbed onto the ion exchange part of the resin with an aqueous solution of an alkali or an acid, to obtain tryptophan containing almost no indole.

The present invention in a second aspect resides in:

a process for recovering indole succeeding to the above process, which comprises eluting indole adsorbed onto the porous part of the resin after elution of tryptophan adsorbed onto the ion exchange part, with a water-containing organic solvent miscible with water.

According to the above processes of the present invention, the resulting tryptophan contains almost no unreacted indole and it is possible to recover indole as an expensive raw material efficiently.

DETAILED DESCRIPTION OF PREFERRED EMBODIMENTS

The reaction fluid of tryptophan used in the present invention refers to e.g. a reaction fluid obtained by enzymatically condensing indole with L-serine in the presence of tryptophan synthase in an aqueous medium, a reaction fluid obtained by casing indole to function with pyruvic acid and ammonia in the presence of tryptophanase, or the like reaction fluid, and those obtained after subjected to a pretreatment such as removal of fungus body protein may also be, of course, used. Further, as far as separation of indole from L-tryptophan as an active ingredient is aimed, the process is not always applied only to the above reaction fluids, but it may also be, of course, applied to a fluid discharged during the purification step such as a filtrate.

As to these fluids such as the reaction fluids, the filtrate, etc., containing the active ingredient, it is preferred to remove therefrom solid substances which may cause clogging of the resin column, in advance of their actual use.

In the process of the present invention, as the ion exchange resin used, if it is a porous type, cation exchange resin, any of those may be used. For example, strongly acidic cation exchange resins of macroporous type are preferred such as Lewatit SP-112 (tradename of product manufactured by Bayer Company), Amberlite 200C (tradename of product manufactured by Rohm and Haas Company), Diaion PK-220 (tradename of product manufactured by Mitsubishi Kasei Company), etc., but even in the case of strongly acidic cation exchange resins, those of gel type cannot be used in the process of the present invention.

The quantity of the resin used is made such a quantity that the total quantity of the cations contained in the fluid to be treated, that is, the total molar equivalent of L-tryptophan and besides, amino acids, ammonium ion, sodium ion, etc. contained usually in the reaction fluid, falls within the total exchange capacity of the resin.

A preferred embodiment in the case where the reaction fluid after the tryptophan reaction is treated, is as follows:

The reaction fluid of tryptophan containing unreacted indole or a filtrate obtained by filtering the above reaction fluid to thereby remove the fungus body contained therein (hereinafter the reaction fluid and the filtrate will be referred to collectively as fluid to be treated), is passed through a layer of porous type, cation exchange resin.

When the fluid to be treated is passed through the layer, its pH is preferred to be neutral to acidic, and the temperature is 90° C. or lower and the passage is carried out at a SV of 1 to 10.

The adsorption and elution of tryptophan onto and from the ion exchange part and the elution of indole adsorbed onto the porous part may be alternately carried out, but there is a large difference between the concentration proportion of tryptophan and that of indole in the fluid to be treated, and also their adsorption mechanisms are different; hence the elution of the adhered indole is preferred to be carried out after the separation treatments of adsorption, elution and regeneration of tryptophan have been repeated a number of times and when the adsorption capacity of indole has been attained.

It is advantageous to carry out the isolation and recovery of indole from the elute according to a process as described above. Thus usually it is preferred to carry out the elution of indole after the adsorption, elution and regeneration of tryptophan have been repeated at least five times, although this depends on the proportion of indole contained. Tryptophan is completely adsorbed through one pass, and while the separation operation thereof is repeatedly carried out, indole is adsorbed and accumulated onto the porous part in the resin; hence when its concentration has reached a constant one, a fluid for eluting indole may be passed to effect is elution, such a treatment affords a high concentration of indole, from which indole is then separated in a conventional manner such as concentration, crystallization or the like, whereby it is possible to easily recover indole of a high purity, and yet the elute of tryptophan during the period contains almost no indole.

The elution of tryptophan adsorbed onto the ion exchange part of the resin is carried out after a fluid to be treated is passed through the resin layer to complete the adsorption of tryptophan, followed each time by passing water therethrough to wash the resin completely. As the fluid for eluting tryptophan, an aqueous solution of an alkali or an acid conventionally used may be used, but aqueous ammonia is preferred. In the case of elution with aqueous ammonia, any of a process wherein 5 to 30% by weight of aqueous ammonia is passed through the column from the upper part thereof at a SV of 1 to 10 to elute tryptophan, a process wherein water in the column is circulated and gaseous ammonia is blown therein and the like process may be employed, and the pH in the column is preferred to be at least 10. Further, although L-tryptophan is almost completely eluted by this operation, it is preferred to push out a remaining portion in the column to recover it.

By such conventional repeated operations, 95% of tryptophan contained in the fluid to be treated is recovered into the resulting elute. Further, indole contained in the fluid to be treated leaks in a slightest quantity into the elute, but if a further purification is required, the elute of L-tryptophan is subjected to a known isolation process i.e. unit operations such as concentration, crystallization, solid-liquid separation, drying, etc., whereby it is possible to isolate a high-quality L-tryptophan containing indole in a desirable tolerable quantity or less.

The resin after elution of tryptophan is fully washed with water, regenerated with hydrochloric acid, sulfuric acid or the like in a conventional manner and repeatedly used.

On the other hand, for eluting indole adsorbed and accumulated onto the porous part of the resin, a water-containing organic solvent is used as a fluid for the elution. With an organic solvent, alone, complete elution is impossible due to its poor affinity with indole. Preferred examples of the organic solvent are lower aliphatic alcohols such as methanol, ethanol, n-propanol, isopropanol, etc. and isopropanol is particularly preferred. From such an alcohol is prepared an aqueous solution of alcohol having an alcohol content of 10% by volume or more, preferably 70% by volume or more, and the solution is passed through the column from its upper part in a quantity of once or more, preferably about twice the quantity of the resin at a SV of 1 to 10 to carry out elution.

The resulting elute of indole may be conventionally concentrated and subjected to solvent recovery, followed by back extraction with a non-aqueous organic solvent such as toluene, hexane, etc., fluid-separation, cooling, crystallization, etc. to obtain solids which are then separated by filtration.

Further, the column after the elution of indole is fully washed with water to remove the solvent and reused for separating tryptophan.

The present invention will be described in more detail by way of Examples.

EXAMPLE 1

Active carbon and water were added to a reacton fluid containing L-tryptophan obtained by condensing indole with L-serine in an aqueous medium in the presence of tryptophan synthase as an enzyme prepared by culturing Escherichia coli, followed by making the pH of the mixture 4 with sulfuric acid, heating at 95°~100° C. for one hour to convert the fungus body into flocs, and thereafter removing the fungus body adsorbed onto the active carbon, as it was, by filtration. The aqueous solution (2,580 g; the total mol equivalent of amino acids and cations, 1.9) obtained by the above pretreatment and containing L-tryptophan (3.8%, 0.19 M), indole (0.1%), L-serine (0.2%, 0.02 M), ammonium ion (0.8%, 0.44 M) and sodium ion (0.2%, 0.09 M) was passed through a column filled with 1 liter of Lewatit SP-112 (tradename of product manufactured by Bayer Company; exchange capacity, 1.9 mol/l) subjected to conditioning regeneration, from the upper part of the column, at a SV of 5. The flowing down fluid after completion of the passage was subjected to to detection of L-tryptophan according to a high speed liquid chromatography. It was not detected.

The resulting resin was washed with water (2 l) at a SV of 10, followed by carrying out elution with 10% aqueous $NH_3$ (600 g) at a SV of 2 and pushing out a remaining portion in the column with water (1,000 g) to obtain an elute (1,600 g). This elute contained L-tryptophan (5.9%; this corresponds to L-tryptophan (94.1 g); percentage recovery based on L-tryptophan in the original fluid to be adsorbed, 96.0%) and indole (1 ppm or less) (percentage of indole removal, nearly 100%).

The elute was concentrated under reduced pressure into about 470 g, followed by crystallizing at 5° C. for 2 hours, filtering in vacuum with Nutsche, further washing with water (100 g) to obtain a wet cake (136.8 g), and drying this cake to obtain yellow-white, scaly crystals (80.4 g).

The overall yield: 82.0%/ original fluid to be adsorbed. As to the quality of the product, purity: 99.6%, angle of rotation: −31.3°, indole content: 1.2 ppm. That is, almost no indole was contained and indole smell was not felt at all. This quality, of course, fully satisfies the standards of additives for domestic feeds.

Further, the resin after elution of L-tryptophan was further washed with water (2 l), followed by passing 80% aqueous propyl alcohol (2,000 g) through the column from its upper part at a SV of 2 to obtain an elute of indole (2,000 g).

This elute contained 0.12% of indole (percentage recovery based on indole in the original fluid to be adsorbed: 92.0%).

EXAMPLE 2

In the same manner as in Example 1 and without carrying out elution of indole, only the adsorption, elution and regeneration of L-tryptophan were repeated 8 times, during which the indole content in the flowing-down fluid at the time of elution of tryptophan was checked and no indole was detected.

In the elute of L-tryptophan at the nineth time was detected a certain quantity of indole; thus, after elution of L-tryptophan at the nineth time, the resin was washed with water, followed by flowing down 80% aqueous isopropylalcohol (2,000 g) from the upper part of the column at a SV of 2 to carry out elution of indole to thereby obtain an elute of indole (2,000 g).

The elute contained 3.2% of indole. The elute was concentrated up to 500 g, followed by adding n-hexane (200 g) at 60° C., mixing, extracting, separating n-hexane layer, cooling, crystallizing at 5° C. for 2 hours, filtering with Nutsche, and drying the resulting wet cake to obtain indole (39.0 g) (percentage recovery: 61.0%, purity according to gas chromatography: 100%). The thus recovered indole was reused as the raw material for the enzyme reaction for L-tryptophan, and the indole was confirmed to have no bad influence upon the reaction.

Further, after completion of such an indole elution, the resulting resin was washed with water and again regenerated, followed by repeating adsorption and elution of L-tryptophan, and when indole was detected in the elute of L-tryptophan, repeating elution and recovery of indole with the aqueous isopropyl alcohol. As a result, with any of the resulting elutes of L-tryptophan, the overall yields were 78.0~84.0%/the original fluid to bn adsorbed, and the indole contents were 3 ppm or less. Even when a long term, continuous operation was carried out as described above, the resulting product was odorless and had a quality which fully satisfies the standards of additives for domestic feeds.

What we claim is:

1. A process for purifying tryptophan which comprises passing a reaction fluid containing tryptophan and unreacted indole, prepared from subjecting indole to an enzyme process, through a porous type of cation exchange resin layer to adsorb tryptophan onto the ion exchange part of the resin while to adsorb indole onto the porous part of the resin, following by eluting tryptophan adsorbed with an aqueous solution of an alkali or an acid.

2. A process according to claim 1 wherein said aqueous solution of an alkali used as the eluent of tryptophan is aqueous ammonia.

3. A process for separating and recovering indole from a reaction fluid containing tryptophan and unreacted indole, prepared from subjecting indole to an enzyme process, which comprises passing the reaction fluid through a porous type of cation exchange resin layer and repeatedly conducting treatments of adsorption of tryptophan onto the ion exchange part of the resin, elution therefrom and regeneration, followed by eluting indole adsorbed onto the porous part of the resin with a water-containing organic solvent miscible with water and isolating indole from the resulting eluate.

4. A process according to claim 3 wherein said water-containing organic solvent miscible with water is an aqueous solution of a lower aliphatic alcohol.

* * * * *

UNITED STATES PATENT AND TRADEMARK OFFICE
CERTIFICATE OF CORRECTION

PATENT NO. : 4,769,474
DATED : September 6, 1988
INVENTOR(S) : Shoichiro Miyahara et al It is certified that error appears in the above-identified patent and that said Letters Patent is hereby corrected as shown below:

```
In the Abstract, line 8, change "absorb" to --adsorb--;
Col. 1, line 60, change "fugus" to --fungus--;
Col. 3, line 23, change "casing" to --causing--;
Col. 4, line 26, change "is" to --its--;
Col. 5, line 24, change "reacton" to --reaction--.
```

Signed and Sealed this

Seventeenth Day of January, 1989

Attest:

DONALD J. QUIGG

Attesting Officer

Commissioner of Patents and Trademarks